United States Patent [19]

Durant et al.

[11] 4,049,671
[45] Sept. 20, 1977

[54] PROCESS FOR PREPARING N-CYANOGUANIDINES

[75] Inventors: Graham John Durant; Charon Robin Ganellin, both of Welwyn Garden City; George Raymond White, Harpenden, all of England

[73] Assignee: Smith Kline & French Laboratories Limited, Welwyn Garden City, England

[21] Appl. No.: 606,268

[22] Filed: Aug. 20, 1975

[30] Foreign Application Priority Data

Sept. 2, 1974 United Kingdom ............... 38258/74

[51] Int. Cl.$^2$ ................. C07D 233/64; C07D 277/38; C07D 249/08; C07D 211/94; C07D 211/96; C07D 211/82; C07D 261/08; C07D 263/32
[52] U.S. Cl. ........................... 548/342; 260/294.8 G; 260/296 AE; 260/296 R; 260/306.8 R; 260/306.8 D; 260/306.8 A; 260/307 R; 260/307 H; 260/308 R; 260/308 H; 548/337

[58] Field of Search ......... 260/309, 294.8 R, 294.8 G, 260/296 R, 296 AE, 306.8 R, 306.8 D, 306.8 A, 307 R, 307 H, 308 R, 308 A

[56] References Cited

U.S. PATENT DOCUMENTS

| 3,876,647 | 4/1975 | Durant et al. | ................. 260/294.8 H |
| 3,897,444 | 7/1975 | Durant et al. | ......................... 260/309 |

FOREIGN PATENT DOCUMENTS

| 2,344,779 | 3/1974 | Germany | |
| 2,433,625 | 1/1975 | Germany | .............................. 260/309 |
| 1,397,436 | 6/1975 | United Kingdom | |

*Primary Examiner*—Natalie Trousof
*Attorney, Agent, or Firm*—Joan S. Keps; Richard D. Foggio; William H. Edgerton

[57] ABSTRACT

Process for preparing N-cyanoguanidines by treating N-(loweralkyl)-N'-cyano-isothioureas with an amine and a heavy metal salt. A specific product is N-cyano-N'-methyl-N''-[2-((5-methyl-4-imidazolyl)methylthio)ethyl]guanidine, useful as a histamine $H_2$-antagonist.

8 Claims, No Drawings

PROCESS FOR PREPARING N-CYANOGUANIDINES

This invention relates to an improved chemical process. In particular it relates to an improved process for the production of certain pharmacologically active guanidine compounds.

In German OLS 2,344,779 and British Patent Specification No. 1,397,436 cyanoguanidine compounds have been described including, inter alia, compounds of the following formula:

FORMULA I

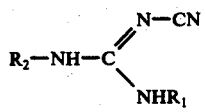

wherein $R_1$ is lower alkyl such as methyl; and $R_2$ is a grouping of the structural shown in Formula II:

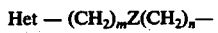

FORMULA II wherein Het is a nitrogen-containing 5 or 6 membered heterocyclic ring such as imidazole, pyridine, thiazole, isothiazole, oxazole, isoxazole, triazole or thiadiazole which is optionally substituted by lower alkyl, hydroxyl, halogen or amino; Z is sulphur, oxygen, or a methylene group; and $m$ is 0, 1 or 2 and $n$ is 2 or 3 such that the sum of $m$ and $n$ is from 2 to 4. Processes for the production of these compounds have also been described therein. One process described was the treatment of a thiourea of formula:

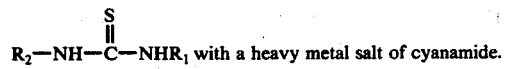

with a heavy metal salt of cyanamide.

The present invention provides an improved process for the production of these compounds. Throughout the specification by the term "lower alkyl" we refer to an alkyl group containing from one to four carbon atoms.

According to the present invention we provide a process for the production of compounds of Formula I wherein an isothiourea of Formula III:

FORMULA III

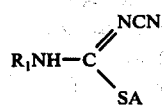

wherein $R_1$ and A which may be the same or different are lower alkyl, for example methyl, is treated with a suitable heavy metal salt and an amine of formula $R_2NH_2$, where $R_2$ has the same significance as in Formula I. By suitable heavy metal salt we mean salts of heavy metals such as silver, mercury, lead or cadmium, and preferably silver nitrate or mercuric chloride. Preferably a base such as potassium carbonate is added to neutralise the acid generated by the reaction. The heavy metal mercaptide which is formed is conveniently removed by filtration. The process of our invention may be carried out in a suitable solvent such as pyridine or dimethylformamide and will proceed at room temperature. Our process therefore offers considerable advantage in terms of reaction rate over the process of the prior art which does not employ a heavy metal salt and may require elevated temperatures and/or extended reaction times. Methods for preparing the amines $R_2NH_2$ are described in British Patent Specifications 1338169 and 1307539. The isothiourea of Formula III may be prepared by the reaction of the known di(lower alkyl)cyanodithioimidocarbonate and a lower alkylamine.

Although we do not wish the present invention to be in any way limited by the following theoretical explanation, we believe that our process proceeds by way of an intermediate carbodiimide of Formula IV:

FORMULA IV wherein $R_1$ has the same significance as in Formula I., (see McCarty et al., J. Org. Chem. 35, 2067, (1970)). On the basis of this belief, our invention also therefore includes a process for the production of compounds of Formula I wherein a carbodiimide of Formula IV is reacted with an amine of formula $R_2NH_2$. Although the preferred method for the production of carbodiimides of Formula IV is from isothioureas of Formula III, we do not wish to be limited, in this aspect of our invention, to this method.

It will be understood that many of the compounds produced and used as starting materials in the process of our invention may exist in the form of an acid addition salt. The process of the present invention is advantageous for the production of compounds of Formula I wherein $R_2$ is Het—$CH_2S$—$(CH_2)_2$ and is particularly preferred when Het is imidazole, thiazole, isothiazole or pyridine and is optionally substituted by methyl, hydroxyl, chlorine or bromine. Specific compounds which may be made by the present process are:

N-cyano-N'-methyl-N"[2-(5-methyl-4-imidazolyl)methylthio)-ethyl]guanidine

N-cyano-N'-ethyl-N"-[2-((5-methyl-4-imidazolyl)methylthio)-ethyl]guanidine

N-cyano-N'-methyl-N"-[2-((5-bromo-4-imidazolyl)-methylthio)-ethyl]guanidine

N-cyano-N'-methyl-N"'-[2-((2-thiazolyl)methylthio)ethyl]guanidine

N-cyano-N'-methyl-N"'-[2-((3-isothiazolyl)methylthio)ethyl]-guanidine

N-cyano-N'-methyl-N"'-[2-((3-hydroxyl-2-pyridyl)-methylthio)-ethyl]guanidine

N-cyano-N'-methyl-N"'-[2-((3-bromo-2-pyridyl)methylthio)ethyl]-guanidine

N-cyano-N'-methyl-N"'-[4-(4-imidazolyl)butyl]guanidine

As stated in German OLS 2,344,779 and British Patent Specification No. 1,397,436 the compounds of Formula I (which may be produced by the present process) are pharmacologically active, for example as histamine $H_2$-antagonists (see Nature 1972, 236, 385), and they are useful for example as inhibitors of gastric acid secretion. For administration they will of course by made up in suitable pharmaceutically acceptable unit dosage forms.

The invention is illustrated but in no way limited by the following examples.

EXAMPLE 1

A solution of N-cyano-N', S-dimethylisothiourea (0.81 g) and silver nitrate (1.06 g) in pyridine (100 ml) was added to a stirred mixture of 2-((5-methyl-4-imidazolyl)methylthio)-ethylamine (1.07 g), anhydrous potassium carbonate (0.44 g) and anhydrous dimethylformamide (4ml). The mixture was stirred at room temperature for 18 hours and filtered. The filtrate was evaporated to dryness and the residue was eluted from a column of silica gel using isopropyl alcoholethylacetate (1:4) followed by isopropyl alcohol-ethyl acetate (1:3) to give N-cyano-N'-methyl-N''-[2-((5-methyl-4-imidazolyl)methylthio)ethyl]guanidine (0.71 g) m.p. 139°–141° C.

EXAMPLE 2

A mixture of N-cyano-N', S-dimethylisothiourea (0.81 g), silver nitrate (1.06 g), anhydrous potassium carbonate (0.44 g) and pyridine (100 ml) was stirred at room temperature for 18 hours and was filtered. The filtrate was evaporated to dryness and was treated with a solution of 2-((5-methyl-4-imidazolyl)methylthio)ethylamine (1.07 g) in dimethylformamide (4 ml) and the mixture was left at room temperature for 18 hours. The mixture was evaporated to dryness and the residue was chromatographed on a column of silica gel, eluting with isopropyl alcohol-ethyl acetate (1:3) to give N-cyano-N'-methyl-N''-[2-((5-methyl-4-imidazolyl)methylthio)ethyl]-guanidine.

EXAMPLE 3

When N-cyano-N'-ethyl-S-methylisothiourea and N-cyano-N'-butyl-S-methylisothiourea are substituted for N-cyano-N', S-dimethylisothiourea in the procedure of Example 1 the products are N-cyano-N'-ethyl-N''-[2-((5-methyl-4-imidazolyl)methylthio)-ethyl]guanidine and N-cyano-N'-butyl-N''-[2-((5-methyl-4-imidazolyl)methylthio)-ethyl]guanidine respectively.

The starting materials may be prepared by treating dimethyldithiocyanoimidocarbonate with ethylamine and butylamine.

EXAMPLE 4

Substitution of 4-(5-methyl-4-imidazolyl)butylamine or 2-(4-imidazolylmethoxy)ethylamine for 2-((5-methyl-4-imidazolyl)-methylthio)ethylamine in the procedure of Example 1 gives N-cyano-N'-methyl-N''-[4-(5-methyl-4-imidazolyl)butyl]guanidine and N-cyano-N'-methyl-N''-[2-(4-imidazolylmethoxy)ethyl]-guanidine respectively.

EXAMPLE 5

Substitution of the following amines:
a. 2-(3-bromo-2-pyridylmethythio)ethylamine
b. 2-(3-chloro-2-pyridylmethylthio)ethylamine
c. 2-(3-hydroxy-2-pyridylmethylthio)ethylamine
d. 2-(2-thiazolylmethlthio)ethylamine
e. 2-(3-isothiazolylmethylthio)ethylamine
f. 3-(2-oxazolylthiopropyl)ethylamine
g. 2-(3-isoxazolylmethylthio)ethylamine
h. 2-(3-(1,2,4)-triazolylmethylthio)ethylamine
i. 2-(5-amino-2-(1,3,4-thiadiazolylmethylthio)ethylamine
j. 2-(5-bromo-4-imidazolylmethylthio)ethylamine for 2-(5-methyl-4-imidazolylmethylthio)ethylamine in the procedure of Example 1, gives a. N-cyano-N'-methyl-N''-[2-((3-bromo-2-pyridyl)-methylthio)-ethyl]guanidine
b. N-cyano-N'-methyl-N''-[2-((3-chloro-2-pyridyl)-methylthio)-ethyl]guanidine
c. N-cyano-N'-methyl-N''-[2-((3-hydroxy-2-pyridyl)-methylthio)-ethyl]guanidine
d. N-cyano-N'-methyl-N''-[2-((2-thiazolyl)methylthio)ethyl]-guanidine
e. N-cyano-N'-methyl-N''-[2-((3-isothiazolyl)methylthio)ethyl]-guanidine
f. N-cyano-N'-methyl-N''-[3-(2-oxazolyl)thiopropyl]-guanidine
g. N-cyano-N'-methyl-N''-[2-((3-isoxazolyl)methylthio)ethyl]-guanidine
h. N-cyano-N'-methyl-N''-[2-(3-(1,2,4-triazolyl)methylthio)-ethyl]guanidine
i. N-cyano-N'-methyl-N''-[2-(2-(5-amino-1,3,4-thiadiazolyl)-methylthio)ethyl]guanidine
j. N-cyano-N'-methyl-N''-[2-((5-bromo-4-imidazolyl)-methylthio)-ethyl]guanidine.

EXAMPLE 6

Substitution of 3-(4-imidazolyl)propylamine and 2-(4-imidazolylethylthio)ethylamine for 2-(5-methyl-4-imidazolylmethylthio)ethylamine in the procedure of Example 1, leads to the preparation of N-cyano-N'-methyl-N''-[3-(4-imidazolyl)propyl]-guanidine and N-cyano-N'-methyl-N''-[2-(4-imidazolylethylthio)-ethyl]-guanidine respectively.

EXAMPLE 7

When N-cyano-N', S-dimethylisothiourea is treated with mercuric chloride in pyridine and the mixture added to a mixture of 2-(5-methyl-4-imidazolyl)methylthio)ethylamine and potassium carbonate in dimethylformamide the product is N-cyano-N'-methyl-N''-[2((5-methyl-4-imidazolyl)methylthio)-ethyl]guanidine.

What we claim is:

1. In a process for the preparatin of a cyanoguanidine of the formula:

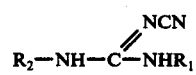

wherein $R_1$ is lower alkyl and $R_2$ is a grouping of structure Het-$(CH_2)_m$Z$(CH_2)$n — wherein Het is an imidazole, pyridine, thiazole, isothiazole, oxazole, isoxazole, triazole or thiadiazole ring, which ring is optionally substituted by lower alkyl, hydroxyl, halogen or amino; Z is sulphur, oxygen or a methylene group; and $m$ is 0, 1 or 2 and $n$ is 2 or 3, such that the sum of $m$ and $n$ is from 2 to 4; in which an isothiourea of the formula:

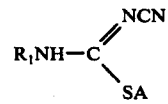

wherein $R_1$ and A, which may be the same or different, are lower alkyl, is treated with an amine of formula $R_2NH_2$ wherein $R_2$ has the same significance as hereinabove, the improvement wherein the reaction is carried out using a suitable heavy metal salt.

2. A process according to claim 1 wherein the heavy metal salt is silver nitrate.

3. A process according to claim 1 wherein the reaction is carried out in the presence of potassium carbonate.

4. A process according to claim 1 wherein the reaction is carried out in pyridine or dimethylformamide.

5. A process according to claim 1 wherein A is methyl.

6. A process according to claim 1 wherein $R_2$ is Het-$CH_2S(CH_2)_2$—.

7. A process according to claim 1 wherein Het is an imidazole, thiazole, isothiazole or pyridine ring, which ring is optionally substituted by methyl, hydroxyl, chlorine or bromine 8. A process according to claim 1 wherein $R_1$ is methyl and $R_2$ is 2-(5-methyl-4-imidazolyl)methylthio)ethyl.

* * * * *